United States Patent [19]

Müller et al.

[11] Patent Number: 5,859,265

[45] Date of Patent: Jan. 12, 1999

[54] OXIDATION CATALYST, ITS PREPARATION AND OXIDATION USING THE OXIDATION CATALYST

[75] Inventors: Ulrich Müller, Neustadt; Peter Lingelbach, Ludwigshafen; Peter Bassler, Viernheim; Wolfgang Harder, Weinheim; Karsten Eller, Ludwigshafen; Veronika Kohl, Münster; Jürgen Dembowski, Göllheim; Norbert Rieber, Mannheim; Martin Fischer, Ludwigshafen, all of Germany

[73] Assignee: Basf Aktiengesellschaft, Ludwigshafen, Germany

[21] Appl. No.: 776,056

[22] PCT Filed: Jul. 7, 1995

[86] PCT No.: PCT/EP95/02651

§ 371 Date: Jan. 21, 1997

§ 102(e) Date: Jan. 21, 1997

[87] PCT Pub. No.: WO96/02323

PCT Pub. Date: Feb. 1, 1996

[30] Foreign Application Priority Data

Jul. 20, 1994 [DE] Germany .............. 44 25 672.8

[51] Int. Cl.$^6$ .............. C07D 301/06; C07D 301/12; B01J 29/06

[52] U.S. Cl. .............. 549/531; 549/533; 502/66; 502/262

[58] Field of Search .............. 549/531, 533; 502/66, 262

*Primary Examiner*—Ba K. Trinh
*Attorney, Agent, or Firm*—Oblon, Spivak, McClelland, Maier & Neustadt, P.C.

[57] ABSTRACT

In an oxidation catalyst based on a titanium or vanadium silicalite having a zeolite structure and containing from 0.01 to 20% by weight of one or more platinum metals selected from the group consisting of ruthenium, rhodium, palladium, osmium, iridium and platinum, the platinum metals are each present in at least two different bond energy states and preferably have no metal-metal bonds.

10 Claims, No Drawings

OXIDATION CATALYST, ITS PREPARATION AND OXIDATION USING THE OXIDATION CATALYST

This application is 371 application of PCT/EP95/02651, dated Jul. 7, 1995.

The present invention relates to a novel oxidation catalyst based on a titanium or vanadium silicalite having a zeolite structure and containing platinum metals, a process for its preparation and various oxidation processes using this oxidation catalyst.

Platinum-containing titanium ailicalites are known to be oxidation catalysts. For example, J.Chem. Soc., Chem.Commun. (1992), 1446–1447 (1) describes the hydroxylation of benzene and hexane over palladium-containing titanium silicalites. Japanese Preliminary Published Application 92/352771 (2) relates to the preparation of propylene oxide from propene, hydrogen and oxygen using a palladium-containing titanium silicalite catalyst.

However, such prior art oxidation catalysts have disadvantages. In many cases, the catalysts are suitable only for a narrow range of intended uses. The selectivity, conversion, space-time yield and life are also often unsatisfactory parameters.

It is an object of the present invention to provide a universally applicable, efficient oxidation catalyst which is easy to prepare and no longer has the disadvantages of the prior art.

We have found that this object is achieved by an oxidation catalyst based on a titanium or vanadium silicalite having a zeolite structure and containing from 0.01 to 20% by weight of one or more platinum metals selected from the group consisting of ruthenium, rhodium, palladium, osmium, iridium and platinum, wherein the platinum metals are each present in at least two different bond energy states.

For the purpose of the present invention, it is of decisive importance that, before it is used, the oxidation catalyst contains the platinum metals in the stated special modification comprising the mixture of different bond energy states. The different bond energy states correspond formally to different oxidation states of the metals. In a preferred embodiment, two, three, four or five different bond energy states are present.

Where two different bond energy states are present, this can represent, for example, a mixture of species of the oxidation states 0 and +1, 0 and +2, 0 and +3 or 0 and +4. The two species are usually present in a ratio of from 5:95 to 95:5, in particular from 10:90 to 90:10.

Where three different bond energy states are present, this can represent, for example, a mixture of species for the oxidation states 0, +1 and +2 or 0, +2 and +3 or 0, +2 and +4 or 0, +1 and +3 or 0, +1 and +4 or 0, +3 and +4. The three species are usually present in a ratio of (0.05–20):(0.05–20):1, in particular (0.1–10):(0.1–10):1.

Furthermore, mixtures of four or more different oxidation states may also be present, for example of 0, +1, +2 and +3 or 0, +1, +2 and +4 or 0, +2, +3 and +4 or 0, +1, +3 and +4 or 0, +1, +2, +3 and +4. Here, the species are present in weight ratios similar to those in the case of the mixtures of 2 or 3 different oxidation states.

The palladium is preferred among the platinum metals. In a particularly preferred embodiment, the palladium is present in two or three different bond energy states.

The bond energy states at the surface of the catalyst may be most simply characterized by X-ray photoelectron spectroscopy (XPS). For example, in a typical mixture of three palladium species, the corresponding values for the energies of the Pd-$3d_{5/2}$ state is 335.0–335.4 eV, 336–336.6 eV and 337.1–337.9 eV, which formally corresponds to the oxidation states $Pd^0$, $Pd^{1+}$ and $Pd^{2+}$.

In the case of the novel oxidation catalysts, it is particularly advantageous to apply the platinum metals in a manner such that no metal-metal bonds are effective and metal-zeolite bonds predominate. In particular, X-ray fine structure investigations (EXAFS) reveal that, with the presence of palladium, an important feature is that virtually exclusively palladium-oxygen bond distances of 2.02±0.02 Å occur and palladium-palladium distances of 2.74±0.02 Å, as in expanded palladium metal or palladium agglomerates, and palladium-palladium distances of 3.04±0.02 Å as in palladium(II) oxide are avoided.

The novel oxidation catalyst is based on known titanium or vanadium silicalites having a zeolite structure, preferably having a pentasil zeolite structure, in particular the types assigned to the MFI or MEL structure or MFI/MEL mixed structure by X-ray analysis. Zeolites of this type are described, for example, in W. M. Meier and D. H. Olson, Atlas of Zeolite Structure Types, Butterworths, 2nd Ed., 1987. Titan-containing zeolites having the ZSM-48, ferrierite or β-zeolite structure are also possible.

In the novel oxidation catalyst, some or all of the titanium of the silicalite may be replaced by vanadium. The molar ratio of titanium and/or vanadium to the sum of silicon plus titanium and/or vanadium is as a rule from 0.01:1 to 0.1:1.

The content of the stated platinum metals in the novel oxidation catalyst is from 0.01 to 20, preferably from 0.1 to 10, in particular from 0.2 to 5%, by weight, based on the total weight of the oxidation catalyst.

In addition to being modified with the stated platinum metals, the novel oxidation catalyst may additionally be modified with one or more elements selected from the group consisting of iron, cobalt, nickel, rhenium, silver and gold. These elements are usually present in an amount of from 0.01 to 10, in particular from 0.05 to 5%, by weight, based on the total weight of the oxidation catalyst.

The novel oxidation catalyst is advantageously prepared by impregnating or reacting a titanium or vanadium silicalite having a zeolite structure with salt solutions, chelate complexes or carbonyl complexes of the platinum metals; in this preparation method, the required distribution of the bond energy states of the platinum metals is established after the impregnation or reaction by suitable reducing or oxidizing conditions.

For example, the platinum metals can be applied, for example, by impregnation with a platinum metal salt solution, in particular in the oxidation states +2 to +4, from pure aqueous, pure alcoholic or aqueous-alcoholic mixture at from 20° to 90° C., in particular from 30° to 55° C. The salts used may be, for example, the corresponding chlorides, acetates or tetramine complexes thereof, and, in the case of palladium, palladium(II) chloride, palladium(II) acetate and the palladium(II)-tetraminechloro complex should be mentioned here. The amount of the metal salts should be chosen so that concentrations of from 0.01 to 20% by weight of platinum metal are achieved on the resulting oxidation catalyst.

The reaction with corresponding chelate complexes of the platinum metals in nonpolar solvents is also suitable here, for example with acetylacetonates, acetonylacetonates or phosphine complexes.

Application in the form of the corresponding carbonyl complexes of the platinum metals is also possible. Here, the procedure is advantageously carried out in the gas phase under superatmospheric pressure or by impregnation with these carbonyl complexes in supercritical solvents, such as $CO_2$.

After any required drying and/or any necessary baking of the resulting catalyst intermediate, the distribution of the bond energy states is preferably established by partial reduction of existing higher oxidation states of the platinum metals, in particular by hydrogenation in a hydrogen atmosphere. If the platinum metals are present in the oxidation state 0, for example when applied as carbonyl complexes, partial oxidation must be carried out.

In a preferred embodiment, the novel oxidation catalyst is impregnated with salt solutions of the platinum metals in the oxidation states +2 to +4 and the dried catalyst is then hydrogenated in a hydrogen atmosphere; in this preparation method, the hydrogenation is carried out at from 20° to 120° C., in particular from 25° to 100° C., especially from 30° to 70° C.

If the temperature is chosen too high in this partial reduction by hydrogenation in a hydrogen atmosphere, the platinum metals are present virtually exclusively in the oxidation state 0, ie. as metals, and in the form of relatively large agglomerates, which is detectable in the micrograph from the occurrence of metal clusters larger than 1.0 nm.

The abovementioned titanium or vanadium silicalites having a zeolite structure, in particular those having an MFI pentasil zeolite structure, are generally prepared by crystallizing a synthetic gel consisting of water, a titanium or vanadium source and silica in a suitable manner with the addition of organic nitrogen-containing compounds (template compounds) under hydrothermal conditions and, if required, with the addition of ammonia, alkali or fluoride as mineralizers. Suitable organic nitrogen-containing compounds are, for example, 1,6-diaminohexane or salts or the free hydroxide of tetraalkylammonium, especially of tetrapropylammonium.

In the preparation of the titanium or vanadium silicalites, contamination with relatively large amounts of alkali metal or alkaline earth metal compounds must be avoided; alkali metal contents (in particular sodium or potassium contents) of <100 ppm are desirable in order subsequently to obtain a sufficiently active oxidation catalyst.

The crystallization of the single-phase structure of the titanium S or vanadium silicalite is preferably effected at 140°–190° C., in particular 160°–180° C., in the course of from 2 to 7 days, a product having good crystallinity being obtained after only about 4 days. The duration of the synthesis on the one hand and the crystallite size on the other hand is substantially reduced by vigorous stirring and a high pH of 12–14 during the crystallization.

For example, primary crystallites of from 0.05 to 0.5 μm, in particular those having a mean particle diameter of less than 0.2 μm, are advantageous.

After the crystallization, the titanium or vanadium silicalite can be filtered off by a method known per se, washed and dried at 100°–120° C.

In order to remove the amine or tetraalkylammonium compounds still present in the pores, the material may furthermore be subjected to a thermal treatment in air or under nitrogen. It is advantageous to burn off the template under conditions which limit the temperature increase to <550° C.

Apart from the abovementioned additions of platinum metals and other elements, the prior art methods of shaping with the aid of a binder, of ion exchange and of surface modification, for example via chemical vapor deposition (CVD) or chemical derivatization, for example silylation, may be used for modifying the novel oxidation catalyst.

The presence of the catalyst functions required for an oxidation reaction can be tested by IR spectroscopy: significant bands occur at 550 $cm^{-1}$ and at 960 $cm^{-1}$ and indicate the presence of the desired crystallinity and of the required oxidation activity.

The novel oxidation catalyst can be effectively used in a number of oxidation reactions. Of particular interest here are the epoxidation of olefins and the preparation of hydrogen peroxide.

The present invention therefore also relates to a process for the preparation of epoxides from olefins, hydrogen and oxygen, when the olefins are reacted under heterogeneous catalysis using the novel oxidation catalyst.

Independently of the olefin to be reacted, the novel epoxidation can be carried out in the liquid phase, in the gas phase or in the supercritical phase. The catalyst is preferably used as a suspension in the case of liquids, whereas a fixed-bed arrangement is advantageous in the gas-phase or supercritical procedure.

If the epoxidation is carried out in the liquid phase, the process is advantageously effected at from 1 to 10 bar and by a suspension procedure in the presence of solvents. Suitable solvents are alcohols, eg. methanol, ethanol, isopropanol or tert-butanol or mixtures thereof, and in particular water. Mixtures of the stated alcohols with water may also be used. In certain cases, the use of water or water-containing solvent systems results in a substantial increase in the selectivity of the desired epoxide compared with the pure alcohols as solvents.

The novel epoxidation is carried out as a rule at from −5° to 70° C., in particular from 20° to 50° C. The molar ratio of hydrogen to oxygen ($H_2:O_2$) can usually be varied in the range from 1:10 to 1:1 and is particularly advantageously from 1:2.5 bis 1:1. The molar ratio of oxygen to olefin is as a rule from 1:1 to 1:3, preferably from 1:1.5 bis 1:1.7. Any inert gas may be introduced as the carrier gas, nitrogen being particularly suitable.

The olefin used can be any desired organic compound which contains at least one ethylenically unsaturated double bond. It may be aliphatic, aromatic or cycloaliphatic and may consist of a linear or branched structure. The olefin is preferably of from 2 to 30 carbon atoms. More than one ethylenically unsaturated double bond may be present, as, for example, in dienes or trienes. The olefin may additionally contain functional groups, such as halogen atoms, carboxyl groups, carboxylic ester functions, hydroxyl groups, ether bridges, sulfide bridges, carbonyl functions, cyano groups, nitro groups or amino groups.

Typical examples of such olefins are ethylene, propene, 1-butene, cis- and trans-2-butene, 1,3-butadiene, pentenes, isoprene, hexenes, octenes, nonenes, decenes, undecenes, dodecenes, cyclopentene, cyclohexene, dicyclopentadiene, methylenecyclopropane, vinylcyclohexane, vinylcyclohexene, allyl chloride, acrylic acid, methacrylic acid, crotonic acid, vinylacetic acid, allyl alcohol, alkyl acrylates, alkyl methacrylates, oleic acid, linoleic acid, linolenic acid, esters and glycerides of such unsaturated fatty acids, styrene, α-methylstyrene, divinylbenzene, inden and stilbene. Mixtures of the stated olefins may also be epoxidized by the novel process.

The novel process is particularly suitable for the epoxidation of propene to propylene oxide.

The present invention also relates to a process for the preparation of hydrogen peroxide from hydrogen and oxygen, wherein the reaction is carried out under heterogeneous catalysis using the novel oxidation catalyst.

As in the case of the novel epoxidation, here too the process can be carried out in the liquid phase by the suspension procedure or in the gas phase or supercritical phase using a fixed-bed arrangement. Regarding the temperature and solvents to be concomitantly used, the statements made there are also applicable. In a system containing containing a carrier gas, the pressure may be up to 100 bar. The molar ratio of $H_2:O_2$ is usually from 1.15 to 1:1, in particular from 1:10 to 1:1.

The novel oxidation catalyst may also be regenerated in a simple manner. Deactivated catalysts can be converted back to an active form by burning off carbon coatings in a controlled manner at from 350° to 650° C., followed by reduction with, for example, hydrogen.

In the case of a small coating, the catalyst can also be regenerated by a simple wash process. Depending on requirements, the wash process can be carried out at neutral, acidic or basic pH. If required, the catalyst activity can also be regenerated by means of a solution of hydrogen peroxide in a mineral acid.

The examples which follow are intended to describe the invention in more detail without restricting it.

EXAMPLE 1

This example describes the crystallization of a titanium silicalite.

For this purpose, 455 g of tetraethyl orthosilicate were initially taken in a 2 l four-necked flask and 15 g of tetraisopropyl orthotitananate were added in the course of 30 minutes from a dropping funnel while stirring (250 rpm, paddle stirrer). A colorless, clear mixture formed. Finally, 800 g of a 20% strength by weight aqueous tetrapropylammonium hydroxide solution (alkali metal content <10 ppm) were added and stirring was continued for a further hour. The alcohol mixture (about 450 g) formed by hydrolysis was distilled off at from 90° to 100° C. The mixture was made up with 1.5 l of demineralized water, and the now slightly opaque sol was transferred to a stirred 2.5 autoclave. The closed autoclave (anchor stirrer, 200 rpm) was brought to a reaction temperature of 175° C. at a heating rate of 3° C./min. The reaction was complete after 92 hours. The cooled reaction mixture (white suspension) was centrifuged and the resulting solid was washed neutral several times with water. The solid obtained was dried at 110° C. in the course of 24 hours (weight obtained 149 g). Finally, the template still present in the zeolite was burnt off under air at 500° C. in the course of 5 hours (loss on calcination: 14% by weight).

The pure white product had a titanium content of 1.5% by weight and a residual alkali metal content (potassium) of <0.01% by weight, according to wet chemical analysis. The yield (based on $SiO_2$ used) was 97%. The crystallite size was about 0.1–0.15 µm and the product showed bands at 960 $cm^{-1}$ and 550 $cm^{-1}$, which are typical for the IR spectrum.

EXAMPLE 2

For impregnation with palladium, a flesh-colored solution was first prepared using 0.515 g of palladium(II) chloride and 120 g of ammonia solution (25% by weight in water) while stirring at room temperature. 60 g of the freshly prepared titanium silicalite from Example 1 were suspended in 130 g of demineralized water in a round-bottomed flask. The total amount of the prepared palladium-tetraminechloro complex solution was added to this, and the mixture was stirred for one hour in the rotary evaporator at room temperature under atmospheric pressure. Finally, the suspension was evaporated down under reduced pressure (5 mbar) at 90°–100° C. The white product was used directly for the reduction.

In a laboratory rotary tubular furnace (quartz glass, diameter 5 cm, length of heating zone 20 cm), 20 g of the Pd-impregnated product were reduced in the course of 90 minutes at 50° C. with a gas mixture comprising 20 l/h of nitrogen and 1 l/h of hydrogen at a rotational speed of the furnace of 50 rpm.

The finished product had a pale color and had no metallic palladium clusters larger than 1.0 nm according to analysis under the transmission electron microscope (TEM). The palladium content was determined at 0.49% by weight by a wet chemical method. The three abovementioned bond energy states of the $Pd-3d_{5/2}$ photoelectron (formally corresponding to the oxidation states +2, +1 and 0) were found by means of XPS. EXAFS measurements on this sample gave a signal for Pd-O or Pd-N bond distances of 2.02±0.02 Å. Pd-Pd bond distances of 2.74±0.02 Å or 3.04±0.02 Å were not observed.

EXAMPLE 3

Using the catalyst from Example 2, the reaction of hydrogen and oxygen to hydrogen peroxide by the suspension procedure at 25°–30° C. was investigated in an explosion-proof pressure resistant apparatus.

For this purpose, 0.1 g of catalyst was suspended in 10 ml of tert-butanol as a solvent in the pressure-resistant reactor and was treated with 0.1 l/min of hydrogen for 30 minutes at room temperature. Thereafter, 40 bar nitrogen was introduced into the reactor and 10 ml/min of hydrogen and 100 ml/min of oxygen were metered in for the duration of 4.5 hours with pressure control. From the total amount of 0.132 mol of hydrogen and 1.32 mol of oxygen, 0.281% by weight of hydrogen peroxide was detected titrimetrically in the reacted mixture by means of iodometry after the pressure had been let down.

When the experiment was repeated in demineralized water as the solvent, a total of 0.196% by weight of hydrogen peroxide was formed from 0.129 mol of hydrogen and 1.29 mol of oxygen.

When methanol was used as the solvent, the reacted mixture contained 0.382% by weight of hydrogen peroxide, formed from 0.129 mol of hydrogen and 1.29 mol of oxygen.

EXAMPLE 4

This example illustrates the one-stage preparation of propylene oxide from propene, hydrogen and oxygen over the catalyst prepared according to Examples 1 and 2, using tert-butanol as the solvent.

In a pressure-resistant glass reactor, 1 g of the catalyst from Example 2 was suspended in 60 ml of tert-butanol as the solvent while stirring and was gassed with 0.45 l/h of hydrogen for 30 minutes, A gas mixture comprising 4 ml/h of propene, 0.45 l/h of hydrogen, 0.45 l/h of oxygen and 1.5 l/h of nitrogen was then passed in at 45° C. and 1 bar.

After 5 hours, gas chromatographic analysis indicated a propene conversion of 0.6% with a selectivity of 90.4% relative to propane and 9.4% relative to propylene oxide.

EXAMPLE 5

This example illustrates the one-stage preparation of propylene oxide from propene, hydrogen and oxygen over the catalyst prepared according to Examples 1 and 2, using methanol as the solvent.

In a pressure-resistant glass reactor, 1 g of the catalyst from Example 2 was suspended in 60 ml of methanol as the solvent while stirring and was gassed with 0.45 l/h of hydrogen for 30 minutes. A gas mixture comprising 4 ml/h of propene, 0.9 l/h of hydrogen, 0.9 l/h of oxygen and 3 l/h of nitrogen was then passed in at 22° C. and 1 bar.

After 17 hours, gas chromatographic analysis indicated a propene conversion of 1.8% with a selectivity of 94.7% relative to propane and 5.2% relative to propylene oxide.

EXAMPLE 6

This example illustrates the one-stage preparation of propylene oxide from propene, hydrogen and oxygen over the catalyst prepared according to Examples 1 and 2, using water as the solvent In a pressure-resistant glass reactor, 1 g of the catalyst from Example 2 was suspended in 60 ml of demineralized water as the solvent while stirring and was gassed with 0.45 l/h of hydrogen for 30 minutes. A gas mixture comprising 4 ml/h of propane, 0.90 l/h of hydrogen, 0.90 l/h of oxygen and 3 l/h of nitrogen was then passed in at 50° C. and 1 bar.

Gas chromatographic analysis indicated a propene conversion of 1.4% with a selectivity of 5.9% relative to propane and 94.0% relative to propylene oxide after 3 hours, a propene conversion of 1.8% with a selectivity of 92.3% relative to propylene oxide after 5 hours and a propene conversion of 1.1% with a selectivity of 91.1% relative to propylene oxide after 20 hours.

We claim:

1. A process for the preparation of epoxides from olefins, hydrogen and oxygen by reaction of the olefins in the presence of heterogeneous catalysts using an oxidation catalyst based on a titanium or vanadium silicalite having a zeolite structure and containing from 0.01 to 20% by weight of one or more platinum metals selected from the group consisting of ruthenium, rhodium palladium, osmium, iridium and platinum, wherein the platinum metals are each present in at least two different bond energy states not containing any effective metal-metal bonds.

2. A process for the preparation of opoxides as claimed in claim 1, using an oxidation catalyst containing from 0.01 to 20% by weight of palladium, wherein the palladium is present in two or three different bond energy states.

3. A process for the preparation of epoxides as claimed in claim 1, using an oxidation catalyst additionally containing one or more elements selected from the group consisting of iron, cobalt, nickel, rhenium, silver and gold.

4. A process for the preparation of epoxides as claimed in claim 1, using an oxidation catalyst having a molar ratio of titanium or vanadium to the sum of silicon plus titanium or vanadium of from 0.01:1 to 0.1:1.

5. A process for the preparation of epoxides as claimed in claim 1, wherein the reaction is carried out in the presence of water.

6. A process for the preparation of epoxides as claimed in claim 1, wherein the olefin is propylene to produce propylene oxide.

7. An oxidation catalyst based on a titanium or vanadium silicalite having a zeolite structure and containing from 0.01 to 20% by weight of one or more platinum metals selected from the group consisting of ruthenium, rhodium palladium, osmium, iridium and platinum, the platinum metals each being present in at least two different bond energy states not containing any effective metal-metal bonds, wherein the titanium or vanadium silicalite has a pentasil zeolite structure assigned to the MFI, MEL or MFI/MEL mixed structure by X-ray analysis.

8. An oxidation catalyst based on a titanium or vanadium silicalite having a zeolite structure and containing from 0.01 to 20% by weight of palladium, the palladium being present in at least two different bond energy states, wherein virtually exclusively palladium-oxygen or palladiumnitrogen bond distances of 2.02±0.02 Å and no palladium-palladium distances of 2.74±0.02 Å and 3.04±0.02 Å occur.

9. A process for the preparation of an oxidation catalyst as claimed in claim 7, or 8 by impregnating or reacting a titanium or vanadium silicalite having a zeolite structure with salt solutions, chelate complexes or carbonyl complexes of the platinum metals, wherein the required distribution of the bond energy states of the platinum metals is established after the impregnation or reaction by suitable reducing or oxidizing conditions.

10. A process for the preparation of an oxidation catalyst as claimed in claim 9 by impregnation with salt solutions of the platinum metals in the oxidation state +2 to +4 and subsequent hydrogenation of the dried catalyst in a hydrogen atmosphere, wherein the hydrogenation is carried out at from 20° to 120° C.

* * * * *